United States Patent [19]

Mack

[11] Patent Number: 4,896,281

[45] Date of Patent: Jan. 23, 1990

[54] METHOD FOR HEAT LOSS SURVEY

[75] Inventor: Russel T. Mack, Lake Jackson, Tex.

[73] Assignee: The Dow Chemical Company, Midland, Mich.

[21] Appl. No.: 239,485

[22] Filed: Aug. 31, 1988

Related U.S. Application Data

[63] Continuation of Ser. No. 739,598, May 31, 1985, abandoned.

[51] Int. Cl.⁴ ............................................. G01K 17/00
[52] U.S. Cl. ...................................... 364/557; 374/121; 374/124
[58] Field of Search .......................... 364/557, 551.01; 374/29, 124, 121, 31; 73/204.11, 198

[56] References Cited

U.S. PATENT DOCUMENTS

| | | | |
|---|---|---|---|
| 4,343,182 | 8/1982 | Pompei | 374/124 |
| 4,372,690 | 2/1983 | Berman et al. | 374/29 |
| 4,372,691 | 2/1983 | Buckley | 374/44 |
| 4,589,781 | 5/1986 | Mack | 374/29 |

Primary Examiner—Parshotam S. Lall
Assistant Examiner—V. N. Trans

[57] ABSTRACT

A method for heat loss surveys comprising the steps of obtaining one or more thermal profiles of a surface radiating heat, the thermal profiles being marked in depicting areas of specified temperatures; at a selected location on each surface a heat flux measurement is made to thereby identify the heat loss from the surface at the selected location. The selected heat loss measurement is then correlated with the thermal profiles by employing a scaling equation to thus obtain indication of heat loss from all increments of the thermal profile, and thence from the entire surface under investigation. Heat loss evaluations for each of the various surfaces of the object being measured are then totalized. The total heat loss and the consequent cost thereof is considered to determine if heat insulation of the object will enhance or impede return on investment.

20 Claims, 6 Drawing Sheets

METHOD FOR HEAT LOSS SURVEY

CROSS-REFERENCE TO RELATED APPLICATION

This is a continuation of application Ser. No. 739,598, filed May 31, 1985 now abandoned.

BACKGROUND OF THE DISCLOSURE

In many different kinds of structures, heat loss or gain can be a serious problem from the standpoint of utility cost. For example, in commercial buildings and dwellings, air conditioning and heating are major cost factors. Also in manufacturing processes in the petroleum, chemical and petrochemical industries, heat transfer can have considerable importance. For purposes of simplicity, however, heat transfer and the need for surveying it is discussed herein particularly in application to industrial processes. Such is not intended to limit the spirit and scope of this invention.

The utility cost of a petrochemical plant can be substantial. A part of the utility cost is occasioned by the necessity of maintaining the process at specified temperatures. As the cost of utilities increases, it becomes expedient to consider applying insulation to reduce heat loss. Insulation of manufacturing process equipment and other structures for heat loss reduction must provide a reasonable return on investment (ROI) to render the provision of insulation commercially feasable. It is generally too costly to simply insulate every exposed surface. Conversely, it is wasteful simply to let a substantial heat flux from the operating petrochemical plant markedly increase the cost of utilities and thus increase the ultimate cost of goods to the consumer.

In the past, heat loss surveys have been conducted mathematically, based on multiple temperature point samples from the object in question and taking into account the ambient temperature at the time of sampling, weather bureau reports of wind direction and velocity, and perhaps other factors as well. These heat loss surveys have been time consuming, expensive, and are subject to many possibilities for error.

Two modes primarily determine the rate of heat loss. That is, heat loss is occasioned by radiation of heat and/or by convection of heat. The radiation loss is particularly important when temperatures approach approximately 400° F. or higher. The loss is substantial at that level, and at higher temperatures. Heat loss by radiation is thus given by the following:

$$Q_r = 0.174 \, E \left\{ \left( \frac{t_s + 459.6}{100} \right)^4 - \left( \frac{t_a + 459.6}{100} \right)^4 \right\} \quad \text{Equation 1}$$

An additional factor is the loss of heat by convection. This refers to the loss of heat as a result of heating the surrounding air. So to speak, an outdoor situated petrochemical plant is an air cooled structure. The rate of convection loss of heat is thus given by:

$$Q_c = 0.296 \, (t_s - t_a)^{5/4} \sqrt{\frac{v = 68.9}{68.9}} \quad \text{Equation 2}$$

which is added to Equation 1 to indicate heat loss by radiation and convection.

In the foregoing equations, the variables are:
E = Emissivity
$t_s$ = surface temperature, degree F
$t_a$ = ambient temperature
v = wind velocity, ft/min
$Q_c$ = convection heat loss, BTU/hr. ft$^2$
$Q_r$ = radiation heat loss, BTU/hr. ft$^2$ Equation 2 (in particular) is not a fundamental or exact equation; it is only one of many (perhaps equally valid) empirical equations for application in different situations—this equation relates to turbulent flow on vertical surfaces. For horizontal surfaces (roofs, for instance) or for very low wind speeds, other equations could be employed for better accuracy. It is not intended that this equation limit the present invention; its provision in this discussion is being provided solely for the purpose of example.

$Q_c$ and $Q_r$ are expressed simply as Q, indicating the rate of heat loss per unit area, BTU/hr—ft$^2$. Surface points chosen at random for the temperature measurement are assumed to represent the average for the system, and Q is simply multiplied by the surface area of the system to calculate overall system heat loss in terms of BTU/hr.

Of the several similar theory-based methods of heat loss measurement which are common in industry at the present time, the above heat loss measurement equation appears to be the most satisfactory. This technique, however, is nevertheless ripe with opportunities for error. For example, a point much hotter or much colder than the surface average can very easily be chosen for the surface point temperature. Also, reported wind velocities seldom accurately represent the local microenvironment of surface convection. Also, adopting $t_a$ as the radiative "sink" temperature is a gross generalization, even if high-temperature equipment in the vicinity is neglected (common in industrial plants). On a clear night, due to the high absorbtivity and cold temperatures of space, the radiative "sink" would probably be much lower than the local air temperature. On a sunny day, obviously, the "sink" temperature would be somewhat higher. A more accurate technique would either avoid the need for assuming a radiative "sink" temperature or would more accurately calculate the sink temperature existing at the time of data collection.

The present invention concerns the principle of obtaining heat loss values for a (relatively) larger area based on an incremental heat loss sample (metered by any suitable means or calculated using traditional convective and/or radiative equations) and an overall temperature profile of the surface under consideration. From the sampled increment, heat losses at other portions of the surface are scaled according to the temperature profile. Increments are summed to provide total heat loss, from which a determination can be made whether the cost of insulating the surface—compared with heat loss savings—will provide an acceptable net return of investment (ROI).

Through suitable infrared photographic techniques, a thermal image of a structure can be obtained. This approach, however, will provide temperature profile lines. Even so, the heat loss is not a simple function of the surface temperature profile alone. Thus, if temperature profile lines are set at a spacing of 20° F. across a surface, merely obtaining such a profile by infrared photographic techniques will not in and of itself provide data to accurately determine the overall heat loss. With the profile and scant additional (easily-collected) data, the two equations could be solved for all elements, and the results summed. In fact, this is done in situations where a fluxmeter cannot be used. Though this is a great improvement over former methods (considering the fact that minute thermal details across the whole surface are rapidly considered) without the use of a fluxmeter, the procedure still has the possibility of significant errors due to the difficulty of obtaining an accurate $t_a$ for Equation 1 and an accurate V for Equation 2 for any point on the surface. For this reason, a measured heat loss sample is obtained from one element of a surface study area whenever possible, and the boundaries of the area are chosen so that every element within the area can reasonably be assumed to have the same E, and be exposed to the same V and radiant $t_a$.

Because there are so many variables involved, the present method simplifies and enables the taking of simple temperature measurements whereby an entire surface area (such as the surface of a petrochemical refining or processing unit) can be evaluated. This method enables heat loss of a structure to be determined typically on a per unit area basis which can be extended to the whole area or to selected portions thereof. The measurement typically provided is total BTU loss for an entire surface and is incrementally defined by BTU loss per surface area and can be obtained for any desired temperature on the surface area. Thus, data and measurements can be obtained for any area, and areas which are too cool to merit further investigation can be discarded.

While the foregoing speaks very generally of the procedure set forth in detail hereinbelow, a better understanding will be obtained upon a review of the following specification with reference to the drawings which are described below.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Three different application catagories for this technology are being researched. These are outlined (Roman numerals) below:

I. Quick Heat Loss Field Surveys

Retrofit surveys can be conducted on a routine basis by a mobile crew without interrupting production. The mobile heat loss survey crew may employ a suitable thermal imager for obtaining an overall thermal image of the heat envelope of an apparatus to aid in measuring heat loss from selected views of the envelope. Such thermal imaging is not intended to limit this invention. Other accurate methods of producing temperature profiles exist, and some may prove useful in particular circumstances. Generally, however, the convenience of thermal imaging is preferred. The accurate heat loss data obtained by this economical method can best be employed for ROI decisions with respect to adding insulation or heat recovery equipment to existing systems.

Procedure

Figure 1:
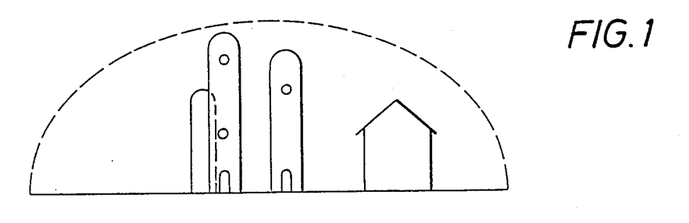
FIG. 1 is a pictorial representation depicting several objects from which heat loss measurements can be obtained, the figure showing the heat influence of the object relative to surrounding structures, including the heat influence of the ground and sky, these being among the number of factors which can impact heat loss of the object.

A. Attention is directed to FIG. 1 of the drawings where a representative setting is shown such as for a petrochemical operating unit and associated buildings and other structures in which heat loss measurements are to be obtained. Any of the structures in the figure may be measured according to the principles of this invention to determine the influence of heat insulation on return of investment (ROI).

The present heat loss measurement procedure implements solutions to the various problems set forth above. For an understanding of the basic heat loss data collection procedure advanced herewith, the following heat loss measurement procedure emphasizes heat loss data collection.

The procedure includes five basic steps which are: (1) preliminary investigation; (2) initial site survey; (3) task layout; (4) data collection; (5) data reduction and final analysis.

Figure 2:
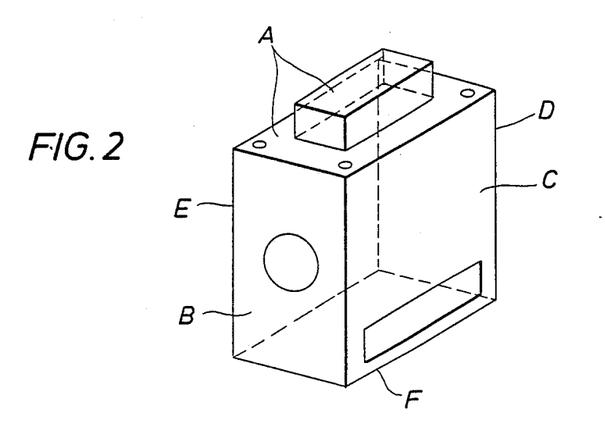
FIG. 2 is a pictorial representation in isometric form, showing a structure to be subjected to heat loss survey.
Figure 3:
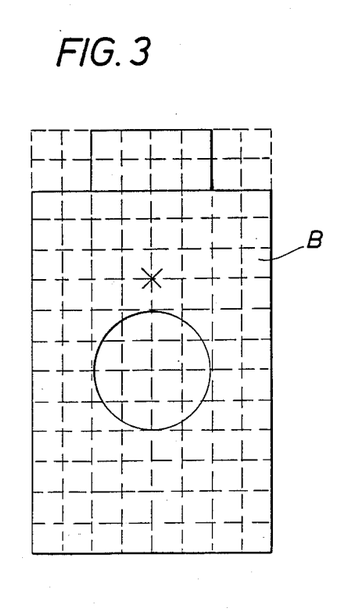
FIG. 3 represents an elevational view of one surface of the structure shown in FIG. 2 and illustrates computer gridding thereof.

(1) During the preliminary investigation, one defines the heat loss "envelope" to be observed or measured, and obtains blueprints or makes sketches identifying the surface area involving the heat loss envelope. FIG. 2 is representative of a structure being subjected to heat loss measurement with surfaces A, B, C, D and E each being considered individually for determination of total heat loss. Any envelope which gains or loses energy by heat transfer—a home, an office building, a utility steam system, a furnace etc.—could be the subject of such a study. In FIG. 2, the subject is a high temperature process reactor.

(2) An initial site survey is conducted to determine areas of similar (not necessarily identical) forward heat loss potential; i.e., areas which are exposed to approximately the same conditions of convection and radiation. For the reactor shown, a separate study is made of each quadrant side (surfaces B through E), plus the top (surface A) and bottom (surface F). The surface emissivity is homogeneous in each of these planes; if it were not homogeneous, the planes would require further subdividing until each surface of study contained only one emissivity. Quantifying the emissivity (a different task)

is not required—one must only define areas where the emissivity appears constant.

(3) In each of the surfaces chosen for direct thermal inspection, a convenient data collection site is marked.

(4) Data collection is conducted by a heat loss audit crew simultaneously with the thermal imaging (or other temperature profiling), collecting data from the data collection sites of each envelope surface, which data includes:

(a) Surface temperature and heat loss ($BTU/ft^2$ at each data collection site).

(b) Ambient temperature a few feet from the surface. To improve accuracy, these flux and temperature readings should be averages of sample values taken at increments of a period of time. Accuracy increases if computer integrated values of data samples are used.

(c) High resolution thermal images of each surface of the envelope are made. To reduce temperature error due to emissivity, a contact pyrometer is placed on a representative part of the surface. The emissivity control on the thermal imager is then adjusted until the image temperature matches the temperature of the contact pyrometer. Areas of uncharacteristic emissivity are spot checked with the surface pyrometer, and corrections noted. (For imagers without emissivity controls, notes would be taken and the adjustments made during data reduction.)

(d) Weather bureau data—including wind speed and temperature at the time of data collection—is also noted, or in the alternative, wind speed and temperature may be simultaneously measured at the data collection site.

(5) Data reduction and final thermal loss analysis are developed in detail as described below.

According to the present invention, a number of innovative principles are provided for effective heat loss data collection and measurement. These principles will be identified as the procedure is explained in a representative sequential manner.

Quick Heat Loss Field Surveys are recommended for rapid and convenient analysis of most exposed (to convection/radiation) heat loss systems such as industrial or commercial systems. The technique is useful for accurately quantifying losses from physical models of thermal systems (or parts of systems). While this procedure is described for a model illustrated as a block, practically all types of structures having a variety of shapes can be analyzed.

B. Salient Features

1. Heat Loss Value From Sample Increment

A primary principle according to the present invention is the principle of obtaining heat loss values for a relatively large area based on an incremental heat loss sample-metered by any means or calculated utilizing traditional convection and/or radiation equations—and an overall temperature profile (collected by any means). From the sample increment, heat loss from other increments is scaled.

Data reduction and reporting may be conducted by means of a computer. Alternatively, data may be recorded for processing through a computer at another location. Data reduction and reporting is as follows:

(a) Assuming a fluxmeter is employed for direct heat loss measurement, heat loss from fluxmeter readings at the individual data collection site are obtained in $BTU/ft^2$-hr.

Note: If the thermal image is computerized and the computer "pixels" are used as the individual elements in the matrix, (b) and (c) may be deleted, and usually (d) will be nearly an automatic function of the computer/software system.

(b) A "rough" heat loss is estimated for a defined larger surface. This is accomplished by multiplying the heat loss from the reference sample site on the surface by the area of the surface.

(c) A large number of elements is used in the finite element analysis to increase the accuracy. However, most computers have a limited amount of data storage space, necessitating a compromise: It is felt that sufficient accuracy can be obtained (for most purposes) by selecting element size such that each element of the envelope represents approximately 0.1% of the total heat loss from the system. The computer automatically divides each surface into elements of correct size. Alternately, this step can be accomplished with a hand calculator and the grid envelope drawn in the fashion of FIG. 2.

(d) Corrected temperatures are assigned to the bands on the thermal images. The thermal images are then superimposed on the envelope matrix, and the surface temperatures are assigned to each surface element. Ideally, this operation takes place as a result of thermal image signals fed directly to the computer to superimpose over the finite element grid.

Figure 4:
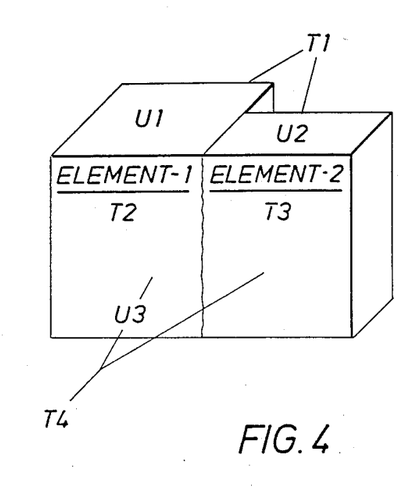
FIG. 4 is a physical representation in isometric form showing heat loss information from a structure for use in mathematical computation of total heat loss from the structure.

(e) An important feature of this technique is the association of elements of similar forward heat loss potential. If the external heat transfer factors (E, V, radiant $t_a$) are similar, then surface temperature differences indicate dissimilarities in internal heat transfer coefficients. Referring now to FIG. 4, a mathematic example of heat loss measurement is depicted wherein:

$T_1$ = internal temp;
$U_1$ and $U_2$ = internal heat transfer coefficients;
$T_2$ and $T_3$ = surface temperatures;
$U_3$ = external heat transfer coefficient; and
$T_4$ = ambient temperature Ignoring time, since $q/A = U\Delta T$, where $$q/A = \frac{\text{heat flow rate}}{\text{unit area}}, \text{BTU/hr} - ft^2$$

$$q/A|_{element 1} = U_3(T_2 - T_4) \text{ and}$$
$$q/A|_{element 2} = U_3(T_3 - T_4),$$

If there is a data collection site in element 1, then heat loss has been determined through that element utilizing a fluxmeter (or other means). To determine the heat loss from element 2, $$\frac{q/A|_{element\ 1}}{U_3(t_2 - t_4)} = 1$$

and $$q/A|_{element\ 2} \simeq (T_3 - T_4) \cdot \left(\frac{q/A|_{element\ 1}}{(T_2 - T_4)}\right)$$

$$q/A|_{element\ 2} \simeq \frac{(t_3 - t_4)}{(t_2 - t_4)} (q/A|_{element\ 1}) \quad \text{Equation 3}$$

$U_3$ cancels because the flux sample site is chosen within a region which appears to have homogeneous forward heat transfer potential—or a same view factor, emissivity, air currents, etc. Error in the heat loss calculation is a smaller function of how well the limits of the region are chosen. For every region where the forward potential is unique, a unique flux sample is best taken to increase accuracy.

$$Qij = Q_{ref\,measured} \left\{ \frac{0.174E\left[\left(\frac{tij + 459.6}{100}\right)^4 - \left(\frac{ta + 459.6}{100}\right)^4\right] + 0.296\,(tij - ta)^{\frac{5}{4}}\left(\sqrt{\frac{V + 68.9}{68.9}}\right)}{0.174E\left[\left(\frac{tref + 459.6}{100}\right)^4 - \left(\frac{ta + 459.6}{100}\right)^4\right] + 0.296\,(tref - ta)^{\frac{5}{4}}\left(\sqrt{\frac{v + 68.9}{68.9}}\right)} \right\}$$

Equation 7

Also it should be noted that Equation 3 results in some error—usually small—due to the over-simplification in the use of $U_3$. In reality, $U_3$ is never a constant; it is a non-linear function of wind speed (not a problem if the area limits are correctly chosen) and temperatures. Since surface temperature variation is expected, errors will occur as a function of the magnitude of the temperature differences within the field.

Since this method will sometimes be employed on surfaces where large temperature differences exist, it is desirable to provide a more exact form. One improvement might be to employ a computer to generate a data set utilizing equation 1 plus equation 2 in addition to equation 3, and applying the resultant pairs of values to a statistical "curve fit" program. Improved overall accuracy results from the following:

$$QA|_{element2} = QA|_{element\,1}\{(8.75_e - 11)\,[T_3(T_3 - T_4)^{0.2}]3.46\}$$

Equation 4 still a fairly simple equation. A multitude of appropriate statistically—derived equations are possible especially since radiation and convection equations other than equation 1 and 2 could be legitimately used to generate initial data. The heat loss data reduction program might even be arranged to select the most appropriate (statistically derived) formula, depending on the magnitudes of Q/A element 1, $T_2$, $T_3$ and $T_4$, and/or the air speed.

The best results, however, have been obtained by treating $U_3$ as non-linear from the beginning, and stating:

$$QA|_{element} = QA|_{element2\,measured}\left(\frac{Q/A|_{element2\,theoretical}}{Q/A|_{element1,theoretical}}\right)$$

Equation 5 or, to be more general:

$$Qij = Q_{ref\,measured}\left(\frac{Qij,\text{theoretical}}{Q_{ref}\,\text{theoretical}}\right)$$

Equation 6 where: i and j represent the row and column matrix # of an unmetered element,

Q = heat loss rate, BTU/hr, and $Q_{ij}$, theoretical and $Q_{ref}$, theoretical are both solved utilizing "textbook" theoretical or emperical equations like Eqn. 1 and 2.

Because Equation 6 is best for scaling the heat losses at unmetered elements from a single metered site, and because it best takes into account the non-linearity of $U_3$, this equation has been standardized for heat loss programs. As a specific example (for turbulent air-flow heat losses from vertical surfaces):

(f) Total heat loss (BTU) is calculated for each envelope surface by summing BTU losses of the individual elements.

(g) Overall heat loss from the entire envelope is calculated by summing the losses from the individual surfaces.

The incremental heat losses may be studied individually or in subgroups. It is most convenient to deal with these increments as elements of definite and specified physical size. From this data, accurate energy cost loss and ROI can easily be calculated using well known formulae.

2. Reference Sample

Another important aspect of the present invention concerns utilization of a contact, thermopile-type thermal fluxmeter or other direct heat loss measuring device to obtain an accurate "reference" heat loss sample for each area for use in the heat loss equations developed under the principle of I., above.

A. A set of Heat Loss Surveys is collected (by the technique described above).

Where a reference site cannot be accessed with a contact pyrometer and a heat-flux measurement device, the thermal profile is generated from optical data and heat flow from each matrix element is solved using equations like 1 and 2—but metered reference samples provide much more reliable results.

Heat fluxmeter devices are available, and one such device is set forth in U.S. Pat. No. 4,589,781 issued May 20, 1986 to R. T. Mack, entitled PORTABLE HEAT FLUXMETER FIXTURES. This device is applied to the surface to measure heat flux. Heat flux is typically given in units of BTU per surface area per hour. This measure is thus obtained at selected locations. Only one of these reference measurements is required for each unique surface emissivity within each image collected. For instance, if the entire object is painted with medium gray alkyd paint (emissivity, about 0.92), and if representative images are collected on the north, south, east, and west sides, then only 4 heat flux samples are required: one sample from each side. If a single image contains an area with somewhat oxidized aluminum insulation sheeting (emissivity, perhaps 0.40) as well as the gray paint, however—then a second flux sample is recommended. This is because it is so inconvenient to exactly quantify emissivities in the field. After field images are reduced to areas of homogeneous emissivities and exposure to (external) convection and/or radiant sources and sinks, heat loss at every unsampled site within individual areas can be scaled from the sampled flux site within the same area using Equation 3, Equation 4 (or some similar statistical form) or an embodiment of general Equation 6—like Equation 7, for instance. Within the same edited area, any sites at the same temperatures as the sampled site (references) will have the same heat loss as the sampled site, as well.

3. Detailed Temperature Profile

Also, the invention concerns utilization of a quantifying infrared thermal imager or a pyroelectric vidicon to obtain a detailed temperature profile for use in the heat loss equations of I., above. A profile heat flux is obtained either by use of traditional convection and radiation formulae, or by the principle of obtaining heat flux values for a larger area based on an incremental heat flux reference sample and an overall temperature profile as mentioned above. Algorithms are then employed which accurately consider the temperature value of each pixel defined on the thermal imager. Treating the pixels as finite elements for use in finite difference, finite element, other matrix forms, or algebraic equations for detailed analysis of all heat flow phenomenon within the system, and in particular for the study of surface heat loss by the method described by the incremental heat loss sample/temperature profile procedure. Editing algorithms to delete pixels outside the area of interest can be employed as well.

Present needs are served by an algorithm which allows specifying some rectangular portion of the overall image for heat loss study, deleting all pixels below and above selected minimum/maximum temperatures of interest and then automatically identifying the unique temperatures within the remaining field, and counting the number of pixels at each unique temperature. Measured reference heat flux and temperature being two input variables, heat flux for the remaining unique temperature zones is calculated according to Equations 3,4,5,6, or 7. Areas can be quantified by several means, (including trigonometrically from input lens angle and distance to the photographic target).

Previously a polar planimeter has been utilized on photographs of temperature profile images (or corresponding slide projections or computer printouts), examining the individual temperature profile bands to obtain areas of each thermal (color) zone. This process is tedious and very time consuming, and according to the present invention the overall area of the study is input and an algorithm calculates the areas of the unique temperatures as a portion of the total area and determines the ratio of the number of pixels in each individual zone to the number of pixels in the overall image. Having the individual areas and the fluxes per unit area, the program computes hourly heat loss from each zone in BTU/hr for the zone. Energy costs are know, and therefore the energy loss per hour is easily calculated. For energy loss and dollar loss per year, several alternatives are available.

$$Q = \frac{(t_1 - t_s)}{R} = \qquad \text{Equation 8}$$

$$0.174E\left[\left(\frac{t_s + 459.6}{100}\right)^4 - \left(\frac{ta + 45.96}{100}\right)^4\right] +$$

$$0.296 (t_s - t_a)^{\frac{5}{4}} \sqrt{\frac{v + 68.9}{68.9}}$$

Here,
Q—heat loss rate
$t_1$ = internal temperature;
$t_s$ = outside surface temperature R = thermal resistance of the wall;
ta = local yearly average temperature; and
V = local average windspeed.

First R is solved (for each pixel) for conditions at the time of the survey. Then the computer solves iteratively for $t_s$ at yearly average conditions, until an accurate $t_s$ is achieved.

Equation 8 provides the hourly heat loss based on local yearly average climate conditions. Yearly heat loss is then simply calculated by multiplying by the yearly operating hours. Notice that many of the problems associated with traditional heat loss calculations seem to have been successfully addressed, but some error can be expected to remain due to inaccuracy in annualized assumptions for the yearly loss projections. In part, this is due to both the radiative sink temperature assumption and to the fact that the equations for convective and radiative losses are not linear, so that loss calculations based on averaged climate conditions can always be expected to be less accurate than loss calculations done at many increments of time and climate conditions. For buildings and other systems near ambient temperature, a more sophisticated algorithm is required to obtain any useful yearly data.

4. Combined Technology of 1, 2 and 3

The features of this invention include combining the subject matter of paragraphs 1, 2 and 3 into an overall heat loss survey technology.

The features hereof also include overall heat loss combining the subject matter of paragraphs 2 and 3 in any fashion to obtain overall heat loss (or heat loss of any increment larger than that sampled by the fluxmeter).

Normally, the procedure outlined above is employed as a *Quick Heat Loss Field Survey*—that is, a one-time, rapid analysis of the heat-loss surfaces. For more demanding problems, an extension of this technology has been developed.

II. Full-range Heat Loss Field Survey

This concept addresses those problems still evident in the technique of Quick Heat Loss Field Surveys. Full-range heat loss surveys can be complex procedures demanding the collection of large amounts of data on several different dates. Total heat survey costs may be high, even for relatively simple systems. For these reasons, this technique is especially useful for those systems which have both a demand for extraordinarily high accuracy of R.O.I. calculation and an expectation of high-dollar returns. In cases where variable convection (wind dependent) are factors, this method is expected to prove useful as well. For all other cases, the Quick Heat Loss Survey technique proves much more practical and economical.

Procedure

A. A set of Heat Loss Surveys is collected (by the techniques described above).

(1) A period of time is chosen when the lowest obtainable stable external temperature (and the highest wind, if this is a facto) exists. Due to the "flywheel effect" common in most industrial thermal systems, climate conditions should be fairly constant for at least three hours before data collection begins, and a complete set of data should be collected before conditions change. To enable accurate data collection:

a. The plant operators should set the internal temperatures (process temperature, room temperature, etc.) to the lowest temperature within the normal operating range, and time should be allowed for the system to stabilize. Then a complete set of heat loss data should be collected along with wind speed and ambient temperature.

b. The plant operators should next set and stabilize temperature at or near the normal internal operating temperature of the plant, and another complete set of heat loss data should be collected.

c. Finally, the plant operators should set and stabilize a temperature at or near the highest internal temperature within the operating range. A third complete set of heat loss data should be collected at this condition.

(2) A second time is then chosen such that external temperatures are stable and near the middle of the normal external temperature range. Three sets of data are collected, as above. This data set should be collected during overcast or partly-cloudy conditions, in the daytime.

(3) A third time is chosen at a time that external temperatures are stable and toward the high end of the normal external temperature range. Three more complete sets of heat loss data are collected, as above. This data set should be collected during sunny conditions.

Data collections at other operating conditions could help to assure greater accuracy. In particular, if the system has a significant wind variation, more data will enhance R.O.I. accuracy.

B. The next step is to produce an image or other graphic representation of the system overlaid with (or otherwise defined by) a finite element matrix with elements of two or more sizes. The element size is adjusted to limit the range of temperatures within any individual element. This is done in order to maintain accuracy of the calculations while reducing computer memory and process time requirements. Usually, the individual elements can be made considerably larger than matrix elements described by the pixel field of the original thermal image data. A computer routine automatically generates a matrix which will produce accurate results, based on the principle of iteratively reducing the size of the elements until each element contains only a specified narrow range of temperatures for either set of the collected data. Obviously, this condition will occur for some elements at a much larger physical size than it will occur for others. To save computer storage space and processing time, a matrix is generated which contains elements of more than one size. Several techniques exist for finite element calculation on matrices with elements of more than one size. For reasons of accuracy and logic, the original set of equations explained below seem to us preferable to earlier methods. (For full range heat loss surveys, only the 2-dimensional forms are required.)

MASSLESS NODE, NON-SEQUENTIAL ASSOCIATION TECHNIQUE

Figure 5:
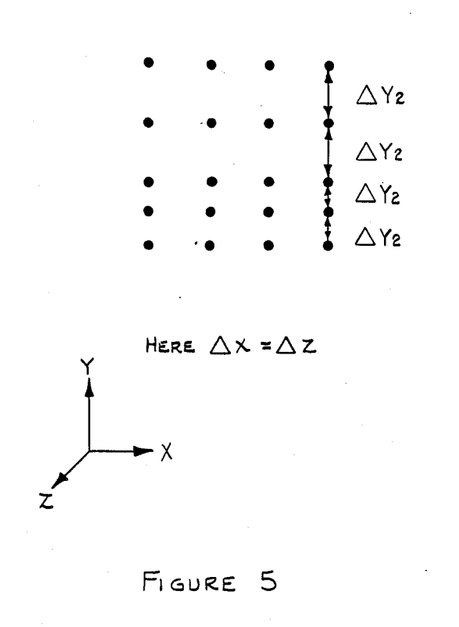
FIGS. 5-12 are graphical illustrations of heat flow analysis in a two or three-dimensional body.

1. If heat flow is being analyzed in a two or three-dimensional body and the need arises to utilize a nodal mesh of two various sizes, the following is proposed (size of nodal mesh changing in one dimension only):

(a) In orthogonal space, at the interface between the two nodal sizes, the distance between the last node of the smaller mesh and the first node of the larger mesh is adjusted to be one-half the normal distance between nodes in the larger mesh (ignoring X and Z dimensions); see FIG. 5.

Figure 6:
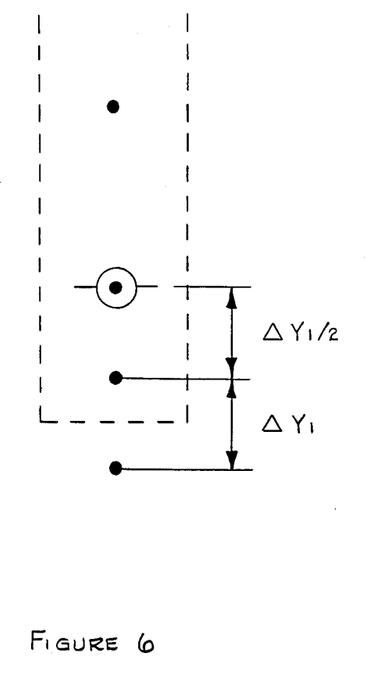

(b) A massless node is inserted between the last node of the smaller mesh and the first node of the larger mesh. The distance between the massless node and the last node of the smaller mesh is adjusted to be one-half the normal distance between nodes in the smaller mesh; see FIG. 6.

Figure 7:
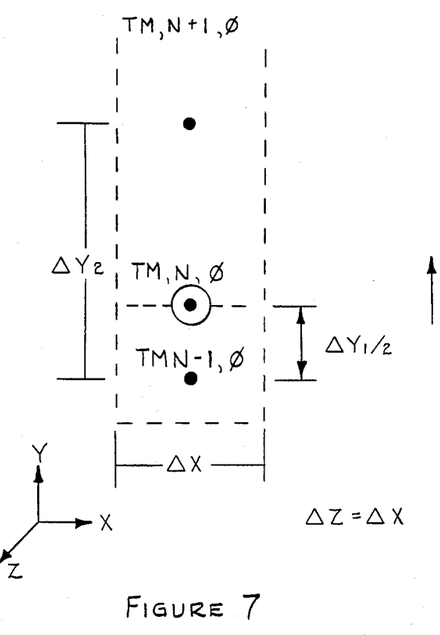

(c) the associated nodal volumes are specified as:
$V_1$ = Volume associated with the last node of the smaller mesh, $= \Delta x \cdot \Delta z \cdot \Delta y_1$, assuming y is the dimension being changed, and
$y_1$ = y-dimension distance between nodes in the smaller mesh.
$V_2$ = The volume associated with the first node of the larger nodal mesh $= (\Delta Y_2 - \Delta Y_{178})$
where $\Delta y_2$ is the y-dimension distance between nodes in the larger mesh; see FIG. 7.

$\Delta Z = \Delta X$

This allows the massless node to be treated exactly like a node in a steady state one dimensional problem. The node is massless; there is no stored heat. Further, since the massless node is on the boundary between the nodal volumes of the first node of the larger mesh and the last node of the smaller mesh, there is no heat flow in X or Z because the area for the heat to flow through is assumed infinitely small at the boundary.

The equation of a massless node associated with changes in nodal mesh is then (for y-direction change):

$$T^{P+1}_{MN\phi} = K\Delta X \Delta Z \left( \frac{T^P_{MN-1\phi} - T^P_{MN\phi}}{0.5\Delta Y_1} + \frac{T^P_{MN+1\phi} - T^P_{MN\phi}}{0.5\Delta Y_2} \right)$$

$$T^P_{MN\phi} = -K\Delta X \Delta Z \left( \frac{T^{P+1}_{MN-1\phi} - T^{P+1}_{MN\phi}}{0.5\Delta Y_1} + \frac{T^{P+1}_{MN+1\phi} - T^{P+1}_{MN\phi}}{0.5 Y_2} \right)$$

Figure 8:
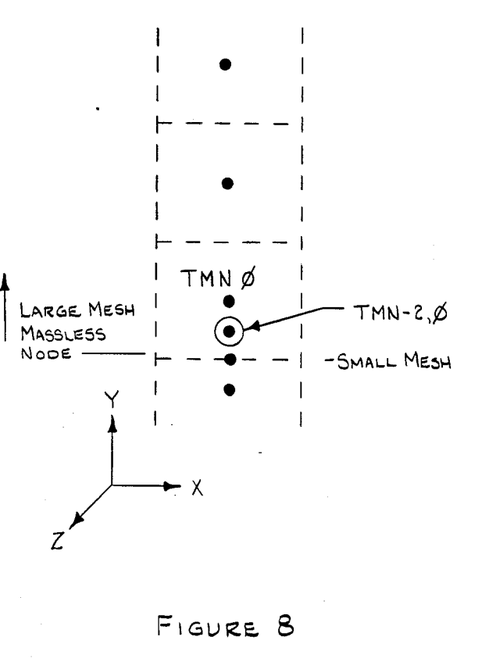

(d) It should be further noted that the index (in the direction of the changed dimension) of the first node of the larger mesh will be non-sequential in order to reference a temperature at the previous node of mass, and the distance coefficient related to the conductivity between the first node of the larger mesh and the last node of the smaller mesh must be halved. This is best illustrated by example shown in FIG. 8, wherein the equation of node $T_{m,n,o}$ is written:

$$T_{MN\phi}^{P+1} = \frac{\alpha \Delta \tau}{[\Delta Y_2/2 + (\Delta Y_2/2 - \Delta Y_1/2)]} \left\{ \Delta Y_2 \left[ \frac{T_{M+1N\phi}^P + T_{M-1N\phi}^P - 2T_{MN\phi}^P}{(\Delta x)^2} \right] + \right.$$

$$\frac{T_{MN+1\phi}^P + T_{MN-1\phi}^P}{\Delta Y_2} + \frac{T_{MN-2\phi}^P - T_{MN\phi}^P}{0.5\Delta Y_2} +$$

$$\left. \Delta Y_2 \left[ \frac{T_{MN\phi+1}^P + T_{MN\phi-1}^P - 2T_{MN\phi}^P}{(\Delta Z)^2} \right] \right\} + T_{MN\phi}^P$$

Care must be taken to make these adjustments to all larger-mesh nodal equations for nodes at the interface between the two mesh sizes.

Figure 9:
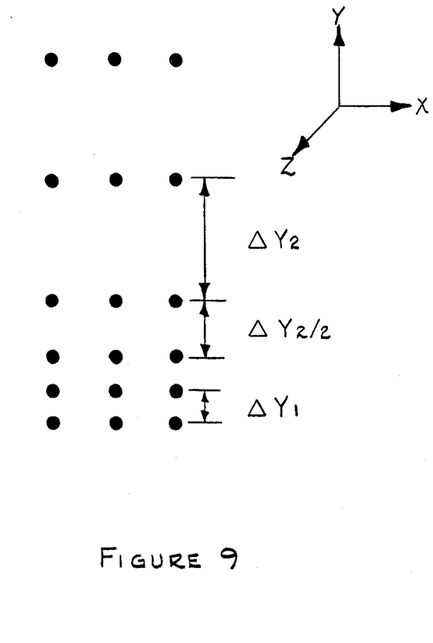

2. Where the size of the nodal mesh is to be changed in two dimensions at once, the procedure is as follows:

(a) The dimension of nodal growth (here the y-dimension) is still used as the control. In this regard, at the interface between the two nodal sizes, the distance between the last node of the smaller mesh and the first node of the larger mesh is adjusted to be one-half the distance between nodes in the larger mesh. Other dimensions (here, $\Delta x$ and $\Delta z$) are the normal distances between nodes in the respective meshes; see FIG. 9.

Figure 10:
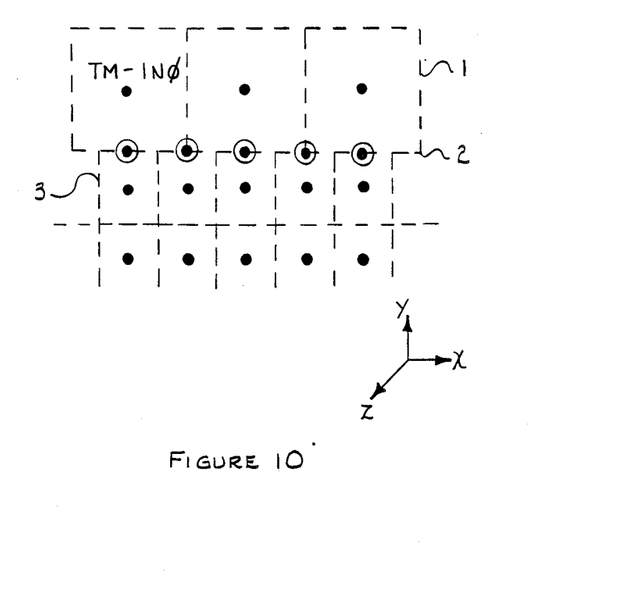

(b) A massless node is inserted between the last node of the smaller mesh and the first node of the larger mesh, exactly as explained in the previous explanation for one dimensional changes (FIG. 10 illustrates the method). At this distance from the last plane of nodes of the smaller mesh (3), a new plane of massless nodes is filled in (2). The element (1) indicates the plane of the larger mesh.

Figure 11:
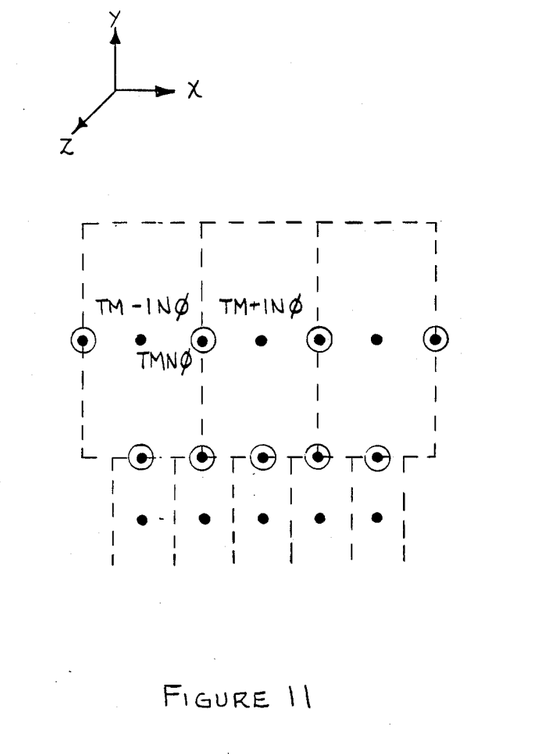

(c) Note that the plane of the remaining dimensions has a nodel mesh twice as dense at the massless node plane as at the corresponding large-mesh plane. This creates the problem of no temperature reference in the direction of the larger mesh for the massless nodes at the corners of the regions. To solve this difficulty, massless nodes are also placed between the nodes in the first plane of the larger mesh, on the boundaries of the associated nodal regions, as shown in FIG. 11.

Heat flow to these new massless nodes is taken as one dimensional, steady state, referenced to the adjacent large mesh nodes.

Example equation in the X dimension:

$$T_{MN\phi}^{P+1} = K\Delta Y_2 \Delta Z \left( \frac{T_{M+1N\phi}^P + T_{M-1N\phi}^P - 2T_{MN\phi}^P}{\Delta X} \right)$$

(d) Heat flow into the corner massless nodes is then described as the sum of the heat flow from the boundary massless node of (3), wherein the distance between the corner massless node and the boundary massless node is obvious, and the area through which the conduction occurs is the normal non reference plane area of the smaller nodal mesh, here $\Delta x_1 \cdot \Delta z_1$, where $\Delta x_1$ and $\Delta z_1$ are the distances between nodes in the smaller mesh-in the x and z dimensions, respectively).

Figure 12:
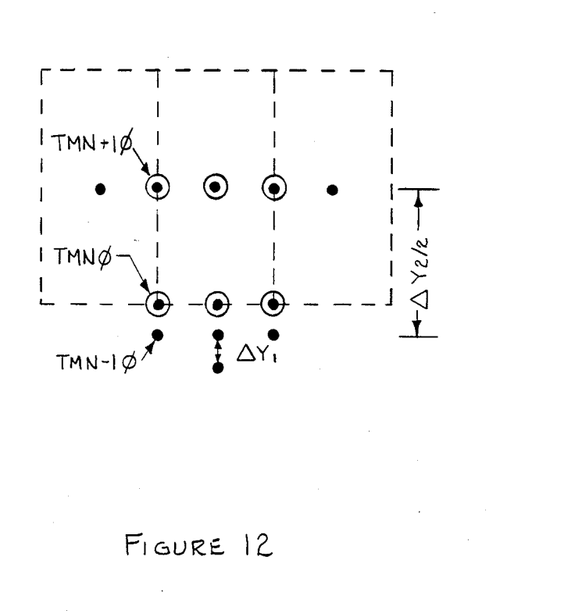
Figure 13:
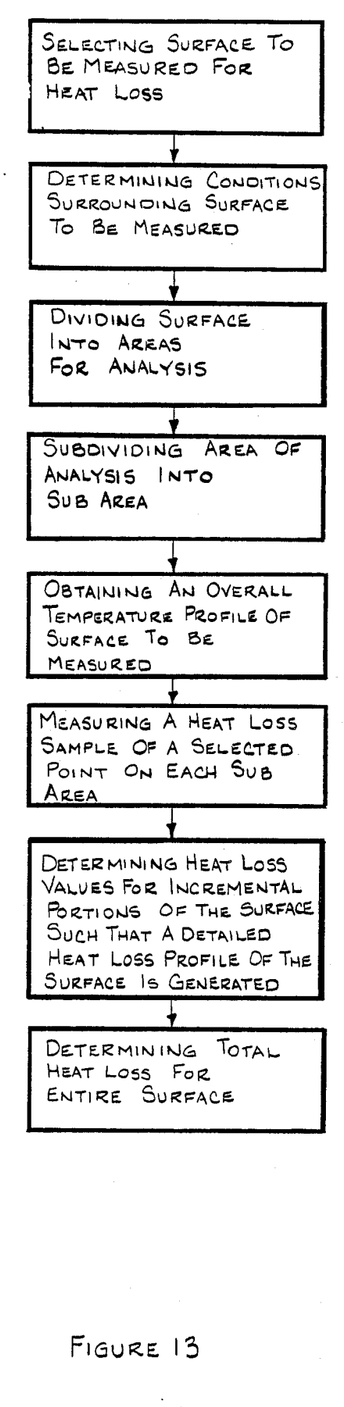
FIGS. 13-18 are schematic flow diagrams of various embodiments of the present invention.
Figure 14:
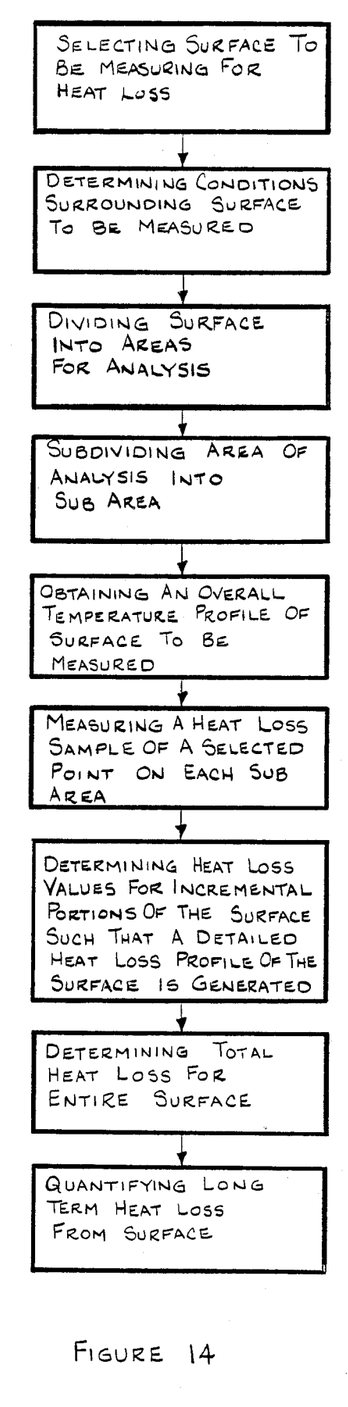
Figure 15:
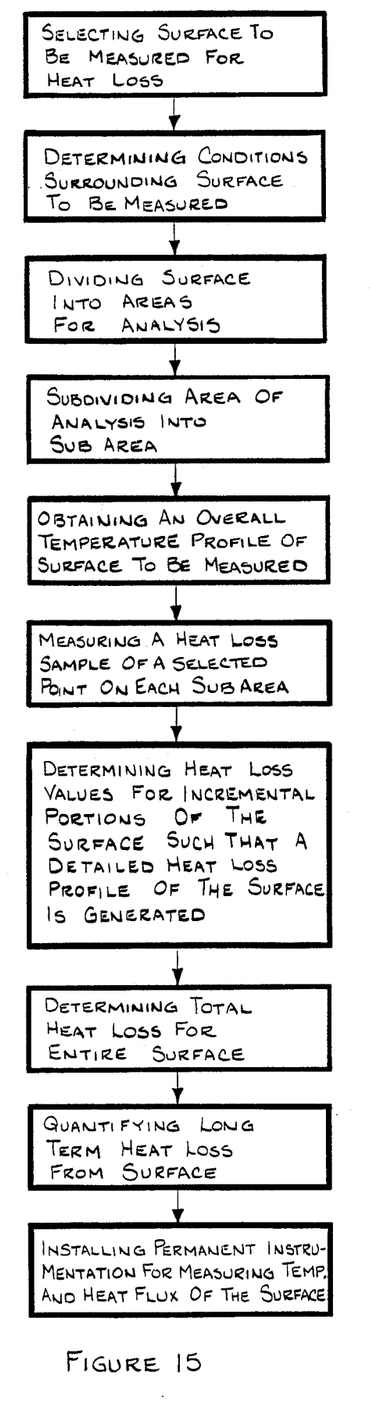
Figure 16:
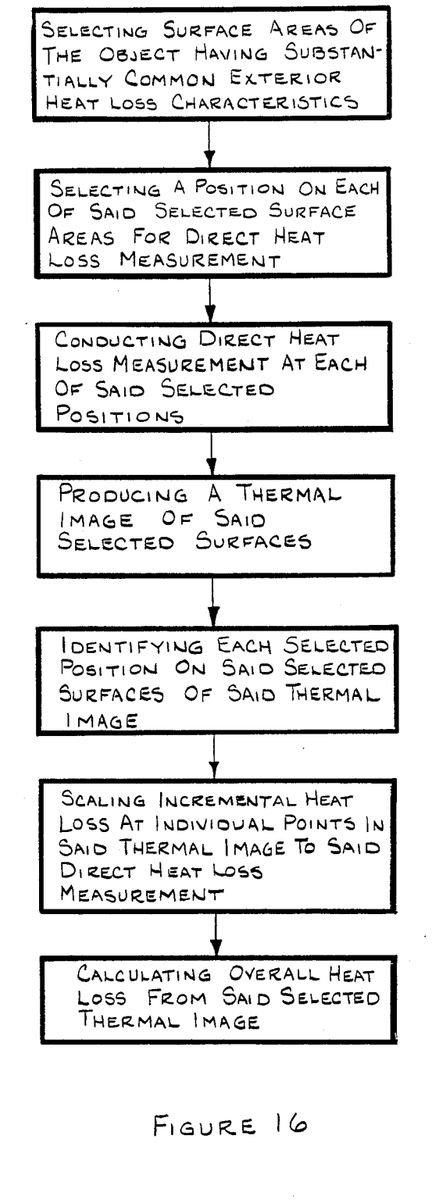
Figure 17:
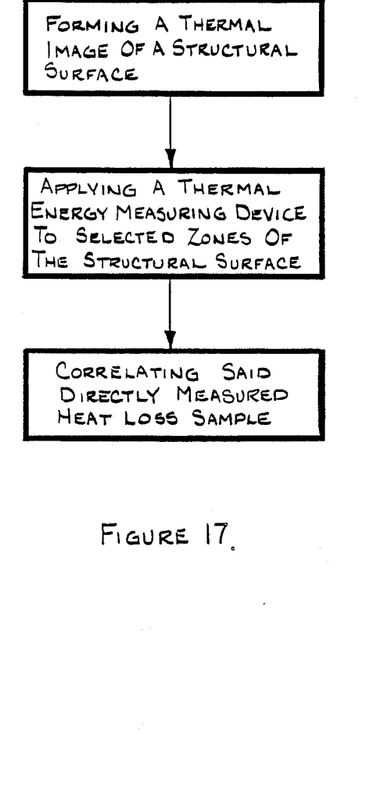
Figure 18:
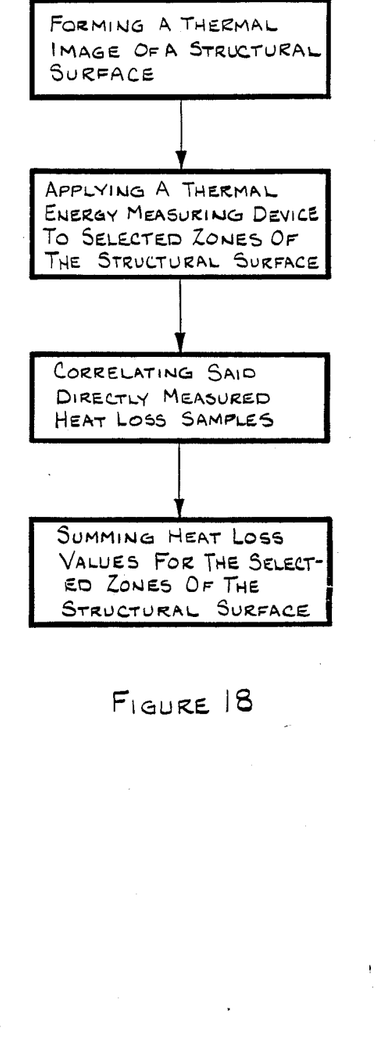

This is described by FIG. 12.

The equation for the corner massless nodes is therefore:

Equation I
$$T_{MN\phi}^{P+1} = K\Delta X_1 \Delta Z_1 \left[ \frac{T_{MN+1\phi}^P - T_{MN\phi}^P}{(\Delta Y_2/2 - \Delta Y_1/2)} + \frac{T_{MN-1\phi}^P - T_{MN\phi}^P}{Y_1/2} \right]$$

Equation II
$$T_{MN\phi}^P = -K\Delta X_1 \Delta Z_1 \left[ \frac{T_{MN+1\phi}^{P+1} - T_{MN\phi}^{P+1}}{(\Delta Y_2/2 - \Delta Y_1/2)} + \frac{T_{MN-1\phi}^{P+1} - T_{MN\phi}^{P+1}}{Y_1/2} \right]$$

Other massless nodes shown are represented with equations like I and II above, and temperature references for large mesh nodes are also as previously shown.

The extension of this technique to simultaneous changes in all three dimensions of nodal size is straight forward. No new equations are required, though the indices will be different for the third dimension.

The obvious limitation is that size changes in the second and third dimensions are restricted to halving (or doubling, as seen progressing from the smaller mesh to the larger). This technique should avoid the inherent error associated with previous methods, especially with regard to mesh changes within layers where a body is made of more than one material.

(C) Next, the matrix developed above (Section B) and the collected data (Section A) is used to generate a new matrix of equations for the solution of Qi, the overall heat loss from the system for any set i of $T_{inside}$, $T_{outside}$, and wind speed.

1. For each element of the matrix, a numerical value for the overall (source to sink) heat transfer coefficient $U_{o,i}$ is quantified for each set of the collected data using the formula $Q_i = U_{o,i} \cdot A \cdot (T_{inside} - T_{outside})$.

2. Variations in U are accommodated using traditional statistical techniques (multiple linear regression, etc.), the collected internal and ambient temperatures, and the fluxes calculated and the numerical U values.

3. The equations are used to form a new matrix for the accurate solution of total heat loss Q.

4. From plant records of the internal operating temperature history, a model of the yearly operating cycle is constructed, and the yearly internal operating temperature history is filed in calendar hour sequence.

5. Local weather history—outside temperatures and wind speed—is researched, and this data is added to the model; again, the data is filed by calendar-hour.

6. For each calendar-hour, total heat loss Q is calculated based on the above data.

7. The annual heat losses are totalled for use in accurate retrofit R.O.I. calculations.

Accuracy of better than 5% in R.O.I. calculations is expected using this method if sufficient local weather data and system operating temperature data is available. Notice that the requirement for an assumed radiative heat sink temperature is eliminated through the extensive data collection procedure.

III. Full Time Heat Loss Monitoring

This method provides an ongoing study of heat loss from a system. A tremendous amount of accurate heat loss data covering a great variety of ambient and operating conditions can be collected conveniently and easily. Two main applications are typical:

A. Applications

1. On prototype equipment, pilot plants, or on any equipment chosen as a basis of study for future improvements, this method will prove to be invaluable in providing management and design teams with accurate and comprehensive heat loss data. For the tradeoff of having to provide a moderate number of permanently installed thermocouples and computer space for monitoring and analysis, equipment owners can be absolutely sure of a thorough understanding of equipment heat loss characteristics under all conditions. This approach is highly recommended in preliminary studies for planned energy intensive plants.

2. Where heat loss is being considered as an operating parameter, this technique can provide industry with data previously unobtainable. Many chemical, petrochemical, and metallurgical production processes, such as for production of electrolytic magnesium, chlorine, titanium and those depending on partial combustion (like coal gasification) share energy balance as a critical operating parameter. Control has often been a problem in these processes, at least partly because of the inability to accurately and continuously monitor radiative and convective heat losses from the system envelope. This new technology facilitates better quality control and better production cost control in energy-balance critical processes.

B. Full Time Monitoring Procedure

1. First, a set of thermal images is taken of the system envelope to include all convective and radiative surfaces. Temperatures need not be quantified, but qualitatively accurate profiles are required.

2. Based on the thermal images and system geometry, permanent monitoring sites are selected. Every area which has a unique forward heat transfer potential—that is, a unique emissivity or radiative or convective exposure—and every exposed side, every protrusion of significant size—is instrumented. Besides the geometric requirements, the thermal profile is considered in that where the temperature profile bands are consistently wide for all data sets, few transducers are required for good accuracy. Where the bands are close together, a higher concentration is called for. Usually, thermocouples are installed at the selected sites.

3. Multiple sets of heat loss data are collected at various operating conditions, as in II.A. above. Reference temperatures are taken from the permanently mounted thermocouples and/or fluxmeters.

4. Heat loss data is determined as in II.B. though II.C., above.

5. Statistical routines (linear regression, etc.) applied to the collected temperature data are employed to produce the temperature at each unmetered matrix element based on the temperatures of nearby metered elements.

6. Using calculated elemental flux for each data set, numerical U values are calculated for each element in the data set.

7. Based on values of temperature and elemental heat loss from 5 and 6, an array for the finite element solution of the overall system heat loss is solved. After this point, heat loss for any instant of time can quickly and automatically be computed, based on instantaneous readings from the permanent thermocouples.

8. Provision can be made for the study of individual surfaces or components of the envelope by adding appropriate subroutines to the computer program.

While the foregoing is directed to the preferred embodiment, the scope is determined by the claims which follow.

What is claimed is:

1. A method for surveys for quantifying immediate heat loss from surfaces, comprising:
   (a) evaluating conditions surrounding the surface for variations in exposure to air flows, sunlight, and other radiant heat sources/sinks and dividing the surface into areas for analysis such that within each area, no significant spatial variation in convective or radiative exposures exists;
   (b) evaluating said areas and further subdividing said areas into sub-areas having unique surface emissivities with no significant inhomogenietys.
   (c) obtaining an overall temperature profile of the surface;
   (d) obtaining a directly measured reference heat loss sample at a selected point on each heat loss sub-area;
   (e) correlating said directly measured heat loss of said reference heat loss sample with said selected point on the surface appearing in said overall temperature profile for development of a detailed heat loss profile of the surface; and
   (f) determining incremental and then total heat loss of the surface.

2. The method according to claim 1 wherein said step of determining total heat loss comprises summing heat loss values for incremental portions of the surface to obtain heat loss values for the entire surface.

3. The method of claim 1 wherein said correlating step is accomplished by scaling heat loss of said overall temperature profile according to directly measured heat loss at selected points on said sub-areas of the surface to thus derive overall heat loss of the surface.

4. The method of claim 1 including quantifying long term heat loss from the surface, comprising:
   (a) evaluating an operating history of the surface and its environment to establish data including ranges of internal operating temperatures, external convective flowrates, external ambient temperatures and external radient heat sources/sinks;
   (b) arranging said data into sets of operating parameters which can statistically provide a comprehensive long term range of heat loss rates for the surface;
   (c) effecting the conditions of each of said sets of operating parameters and conducting a heat loss survey;
   (d) establishing the period of time for which the total heat loss will be modeled; and
   (e) checking the operating history and multiplying the total heat losses of each survey of said surface established by a weighting factor-relative to the fraction of the total modeled time and the portion of said modeled time that each set of operating parameters represents.

5. The method of claim 4 wherein permanently-installed instrumentation and full-time heat loss monitoring capability is provided, comprising:
   (a) collecting a set of temperature profiles as recited in (a) through (c) of claim 4 with no heat loss readings being taken;
   (b) based on the constraints of (a) and (b) of claim 1, dividing the surface into areas of analysis, each of said areas of analysis being permanently instrumented with means for direct temperature measurement and/or means for direct heat flux measurement devices;
   (c) collecting multiple sets of heat loss data according to (a) through (c) of claim 4; and
   (d) developing a comprehensive heat loss profile for each set of operating conditions;
   (e) conducting statistical routines applied to the collected temperature data, and said statistical routines being employed to produce the temperature at each unmetered matrix element based on the temperatures of nearby metered elements;
   (f) using calculated elemental flux for each data set, calculating numerical U values for each element in the data set;
   (g) solving an array for the finite element solution of the overall system heat loss based on values of temperature and elemental heat loss from (e) and (f) of claim 5;
   (h) selectively subdividing a said array into heat loss from any individual surface or other set of elements; and
   (i) following preparation according to (a) through (h) of claim 5, calculating and reporting heat loss for any instant of time, said calculating and reporting being computer generated within seconds after an instantaneous sampling of the temperatures at the permanent thermocouple sites.

6. The method of claim 5, wherein a plurality of instrumentation sites are located within selected areas of said surface having steep temperature gradients.

7. The method of claim 5, wherein
   (a) heat measurement devices are permanently installed at selected locations on said surface; and
   (b) collecting heat flux samples is accomplished by portable heat flux measurement devices.

8. A method for conducting heat loss surveys to obtain the heat loss at selected surfaces of objects, comprising:
   (a) selecting surface areas of the object having substantially common exterior heat loss characteristics;
   (b) selecting a position on each of said selected surface areas for direct heat loss measurement;
   (c) conducting direct heat loss measurement at each of said selected positions;
   (d) producing a thermal image of said selected surfaces;
   (e) identifying each selected position on said selected surfaces of said thermal image;
   (f) scaling said thermal image to said direct heat loss measurement; and
   (g) calculating overall heat loss from said selected thermal image.

9. A method as recited in claim 8 wherein said thermal image presents heat loss variations in the form of colors representing temperature ranges.

10. A method as recited in claim 9 wherein scaling is accomplished by comparing the heat loss of said selected position as appearing on the thermal image and determining the various heat loss rates represented by all of the color variations as the result of said comparison.

11. A method as recited in claim 10 wherein said calculating step comprises summing the heat loss represented by the areas encompassed by each range of heat loss represented by said colors of said thermal image.

12. A method for surveying thermal losses from structural surfaces, comprising:
   (a) forming a thermal image of a structural surface by infrared imaging of the structural surface with an infrared imaging apparatus, said image comprising a radiant energy sensitive film exposure wherein the imaged structural surface is subdivided to radiant energy zones depicting structural surface temperature variations;
   (b) applying a thermal energy measuring device to selected zones of the structural surface to obtain directly measured reference heat loss samples at said selected zones; and
   (c) correlating said directly measured heat loss samples from step (b) taken at said selected zones with said structural surface temperature variation in said radiant energy zones of step (a) to obtain a thermal energy loss profile of the structural surface measured in thermal energy loss per unit of time.

13. The method according to claim 12 including summing heat loss values for the selected zones of the structural surface to obtain heat loss values for the entire surface.

14. The method of claim 12 wherein said correlating step is accomplished by scaling heat loss of said selected zones according to directly measured heat loss at selected points on said zones of the surface to thus derive overall heat loss of the structural surface.

15. The method of claim 12 wherein:
   (a) step (a) includes selecting surface areas of the structural surface having substantially common exterior heat loss characteristics and producing a thermal image of said selected surface area;
   (b) step (b) includes selecting a position on each of said selected surface areas for direct heat loss measurement and producing a thermal image of said selected surface areas;
   (c) step (b) includes identifying each selected position on said selected surfaces of said thermal image; and
   (d) step (c) includes scaling said thermal image to said direct heat loss measurement calculating overall heat loss from said selected thermal image.

16. The method of claim 15 wherein a plurality of instrumentation sites are located within selected areas of said surface having steep temperature gradients.

17. A method of claim 16, wherein
   (a) heat measurement devices are permanently installed at selected locations on said surface; and
   (b) the collecting of heat flux samples is accomplished by portable heat flux measurement devices.

18. The method of claim 15 wherein said thermal image presents heat loss variations in the form of colors representing temperature ranges.

19. A method as recited in claim 18 wherein scaling is accomplished by comparing the heat loss of said selected position as appearing on the thermal image and determining the various heat loss rates representing by all of the color variations as the result of said comparison.

20. The method of claim 19 wherein said calculating step comprises summing the heat loss represented by the areas encompassed by each range of heat loss represented by said colors of said thermal image.

* * * * *

UNITED STATES PATENT AND TRADEMARK OFFICE
CERTIFICATE OF CORRECTION

PATENT NO. : 4,896,281
DATED : January 23, 1990
INVENTOR(S) : Russel T. Mack

It is certified that error appears in the above-identified patent and that said Letters Patent is hereby corrected as shown below:

Column 7, Line 34; add a dash after the "possible".

Column 9, Line 49; change "know" to --known--.

Column 9, Line 55-63; in Equation 8 correct all three occurrences of "t5" to read as --$t_s$--, and correct "45.96" to read as --459.6--.

Column 10, Line 61; change "facto" to --factor--.

Column 12, Line 16; the equation should be changed to read $$( \triangle Y_2 - \triangle Y_{\frac{1}{2}} )$$

Column 12, line 21-32; equation II should be change to read

UNITED STATES PATENT AND TRADEMARK OFFICE
CERTIFICATE OF CORRECTION

PATENT NO. : 4,896,281

DATED : January 23, 1990

INVENTOR(S) : Russel T. Mack

It is certified that error appears in the above-identified patent and that said Letters Patent is hereby corrected as shown below:

Column 12, Line 45-59; the equation should be changed to read $$T_{MN\emptyset}^{P+1} = K\Delta X \Delta Z \left( \frac{T_{MN-1\emptyset}^{P} - T_{MN\emptyset}^{P}}{0.5\Delta Y_1} + \frac{T_{MN+1\emptyset}^{P} - T_{MN\emptyset}^{P}}{0.5\Delta Y_2} \right)$$

$$T_{MN\emptyset}^{P} = -K\Delta X \Delta Z \left( \frac{T_{MN-1\emptyset}^{P+1} - T_{MN\emptyset}^{P+1}}{0.5\Delta Y_1} + \frac{T_{MN+1\emptyset}^{P+1} - T_{MN\emptyset}^{P+1}}{0.5 Y_2} \right)$$

Column 13, Line 1-16; the equation should be changed to read $$T_{MN\emptyset}^{P+1} = \frac{\alpha \Delta \tau}{[\Delta Y_2/2 + (\Delta Y_2/2 - \Delta Y_1/2)]} \left\{ \Delta Y_2 \left[ \frac{T_{M+1N\emptyset}^{P} + T_{M-1N\emptyset}^{P} - 2T_{MN\emptyset}^{P}}{(\Delta X)^2} \right] + \right.$$

$$\frac{T_{MN+1\emptyset}^{P} + T_{MN-1\emptyset}^{P}}{\Delta Y_2} + \frac{T_{MN-2\emptyset}^{P} - T_{MN\emptyset}^{P}}{0.5 \Delta Y_2} +$$

$$\left. \Delta Y_2 \left[ \frac{T_{MN\emptyset+1}^{P} + T_{MN\emptyset-1}^{P} - 2T_{MN\emptyset}^{P}}{(\Delta Z)^2} \right] \right\} + T_{MN\emptyset}^{P}$$

UNITED STATES PATENT AND TRADEMARK OFFICE
CERTIFICATE OF CORRECTION

PATENT NO. : 4,896,281

DATED : January 23, 1990

INVENTOR(S) : Russel T. Mack

It is certified that error appears in the above-identified patent and that said Letters Patent is hereby corrected as shown below:

Column 13, Line 51-56; the equation should be changed to read $$T_{MN\emptyset}^{P+1} = K \Delta Y_2 \Delta Z \left( \frac{T_{M+1N\emptyset}^{P} + T_{M-1N\emptyset}^{P} - 2T_{MN\emptyset}^{P}}{\Delta X} \right)$$

Column 13, Line 58; after "the" insert -- adjacent small mesh node and the heat flow from the --.

Column 13, Line 64; change "mesh-in" to read -- mesh in --.

UNITED STATES PATENT AND TRADEMARK OFFICE
CERTIFICATE OF CORRECTION

PATENT NO. : 4,896,281
DATED : January 23, 1990
INVENTOR(S) : Russel T. Mack It is certified that error appears in the above-identified patent and that said Letters Patent is hereby corrected as shown below:

Column 14, Line 16-20; equation I should be changed to read

Equation I $$T_{MN\phi}^{P+1} = K \Delta X_1 \Delta Z_1 \left[ \frac{T_{MN+1\phi}^{P} - T_{MN\phi}^{P}}{(\Delta Y_2/2 - \Delta Y_1/2)} + \frac{T_{MN-1\phi}^{P} - T_{MN\phi}^{P}}{Y_1/2} \right]$$

Column 14, Line 21-24; equation II should be changed to read

Equation II $$T_{MN\phi}^{P} = -K \Delta X_1 \Delta Z_1 \left[ \frac{T_{MN+1\phi}^{P+1} - T_{MN\phi}^{P+1}}{(\Delta Y_2/2 - \Delta Y_1/2)} + \frac{T_{MN-1\phi}^{P+1} - T_{MN\phi}^{P+1}}{Y_1/2} \right]$$

Signed and Sealed this

Tenth Day of September, 1991

*Attest:*

HARRY F. MANBECK, JR.

*Attesting Officer*     *Commissioner of Patents and Trademarks*